United States Patent
Heaven

(10) Patent No.: US 10,959,831 B2
(45) Date of Patent: Mar. 30, 2021

(54) SYSTEM AND METHOD FOR SECURING TISSUE TO BONE

(71) Applicant: Conmed Corporation, Utica, NY (US)

(72) Inventor: Malcolm Heaven, Reno, NV (US)

(73) Assignee: Conmed Corporation, Utica, NY (US)

( * ) Notice: Subject to any disclaimer, the term of this patent is extended or adjusted under 35 U.S.C. 154(b) by 185 days.

(21) Appl. No.: 16/105,478

(22) Filed: Aug. 20, 2018

(65) Prior Publication Data

US 2018/0353282 A1 Dec. 13, 2018

Related U.S. Application Data

(62) Division of application No. 14/727,410, filed on Jun. 1, 2015, now Pat. No. 10,080,647, which is a division of application No. 13/269,460, filed on Oct. 7, 2011, now Pat. No. 9,044,313.

(60) Provisional application No. 61/391,554, filed on Oct. 8, 2010.

(51) Int. Cl.
*A61F 2/08* (2006.01)
*A61B 17/04* (2006.01)
*A61B 17/00* (2006.01)

(52) U.S. Cl.
CPC ........ *A61F 2/0811* (2013.01); *A61B 17/0401* (2013.01); *A61F 2/0805* (2013.01); *A61B 2017/0046* (2013.01); *A61B 2017/00526* (2013.01); *A61B 2017/00911* (2013.01); *A61B 2017/0403* (2013.01); *A61B 2017/0409* (2013.01); *A61B 2017/0432* (2013.01); *A61B 2017/0433* (2013.01); *A61B 2017/0445* (2013.01); *A61B 2017/0458* (2013.01); *A61F 2002/0835* (2013.01); *A61F 2002/0841* (2013.01); *A61F 2002/0858* (2013.01); *A61F 2002/0882* (2013.01); *A61F 2002/0888* (2013.01)

(58) Field of Classification Search
CPC ...... A61B 17/04; A61B 17/0401; A61B 17/22
USPC ....... 623/13.11–13.16; 606/62–64, 232, 286, 606/300–304, 309–313; 604/399
See application file for complete search history.

(56) References Cited

U.S. PATENT DOCUMENTS

| | | | |
|---|---|---|---|
| 6,533,816 B2 * | 3/2003 | Sklar | A61F 2/0811 623/13.14 |
| 7,828,802 B2 * | 11/2010 | Levy | A61B 17/68 606/300 |
| 2006/0229617 A1 * | 10/2006 | Meller | A61B 17/746 606/62 |

* cited by examiner

Primary Examiner — Yashita Sharma
(74) Attorney, Agent, or Firm — Bond, Schoeneck & King, PLLC; Frederick J.M. Price

(57) ABSTRACT

Disclosed herein are methods and devices for securing soft tissue to a rigid material such as bone. A tissue anchoring device is described that comprises an anchor body and a spreader such that tissue may be captured or compressed between outside surfaces on the anchor and inside surfaces of a bone tunnel to secure the tissue within the tunnel. An anchoring device is described that comprises an anchor body having compressible tabs with teeth, and a spreader that forces the compressible tabs into an expanded state when inserted into anchor body, facilitating engagement between bone and the teeth of the compressible tabs. Methods are described that enable use of the bone anchoring device to secure a tissue graft into the tibial and femoral bones during anterior cruciate ligament ("ACL") reconstruction.

15 Claims, 21 Drawing Sheets

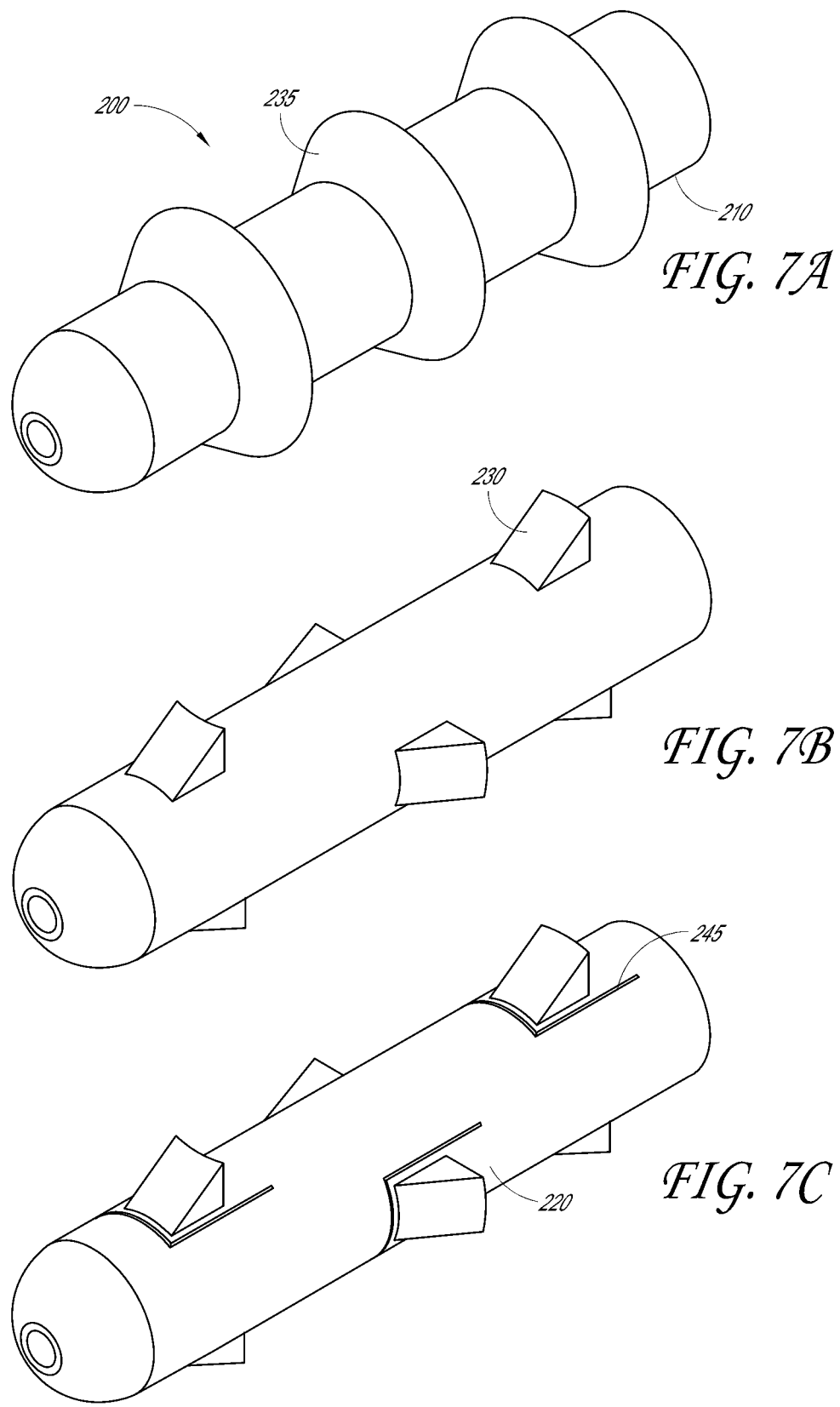

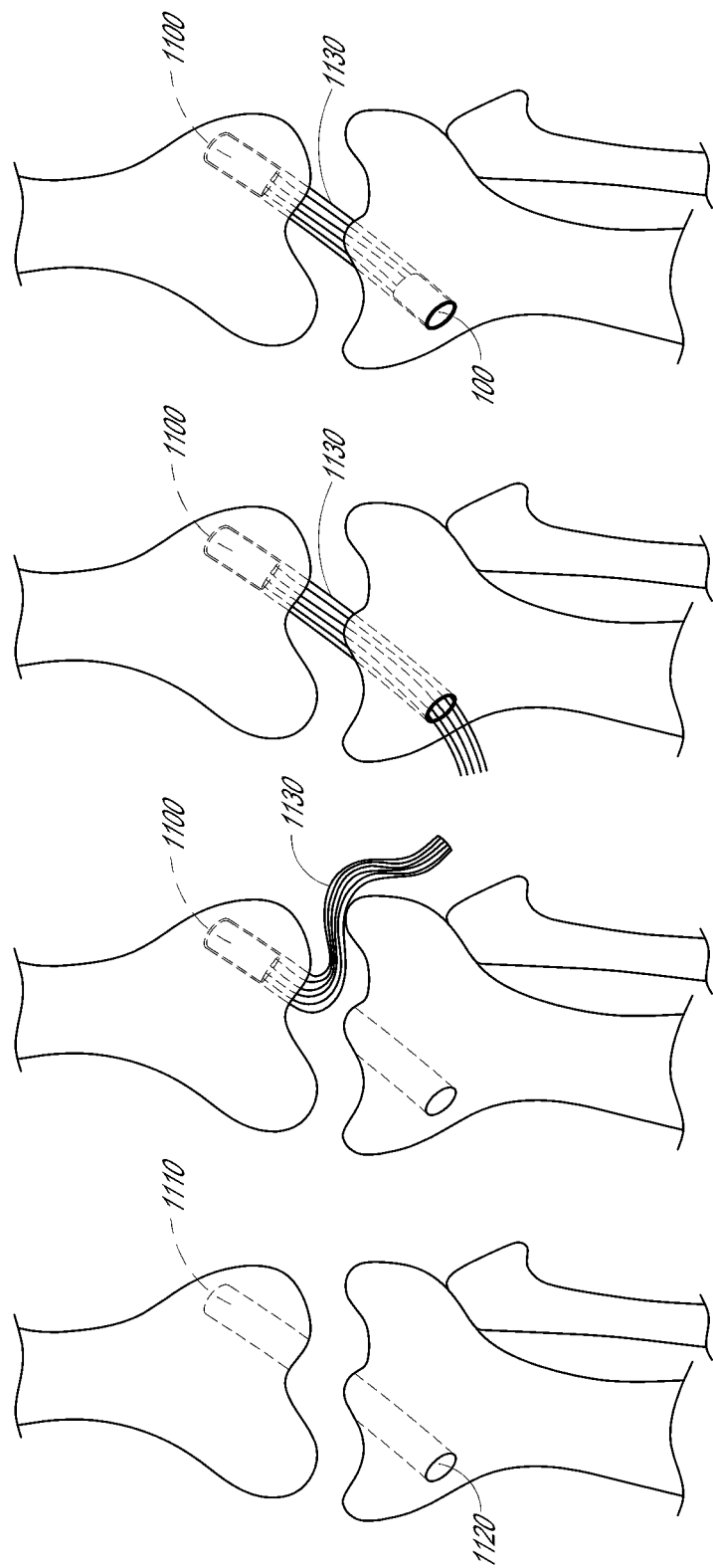

SYSTEM AND METHOD FOR SECURING TISSUE TO BONE

CROSS-REFERENCE TO RELATED APPLICATIONS

This application is a divisional of U.S. application Ser. No. 14/727,410 filed Jun. 1, 2015, which is a divisional of U.S. application Ser. No. 13/269,460, filed Oct. 7, 2011 which is now U.S. Pat. No. 9,044,313, which claims priority to U.S. Provisional Application No. 61/391,554, filed on Oct. 8, 2010, each of which is incorporated herein by reference in its respective entirety.

BACKGROUND OF THE INVENTION

1. Field of the Invention

The present invention relates to medical devices and procedures. More particularly, the present invention relates to devices and methods for securing soft tissue to a rigid material such as bone. Systems and methods are disclosed herein of fixing tissue such as tendon or ligament to bone in orthopedic procedures.

2. Description of the Related Art

There are several medical procedures where a surgeon needs to attach soft connective tissue such as tendons or ligaments to bone. One common example is an anterior cruciate ligament ("ACL") reconstruction, a surgical procedure usually performed for the treatment of a torn ACL. The ACL is one of four major ligaments of the knee. An ACL reconstruction may be performed as an isolated procedure, but is often performed alongside the treatment of meniscus tears and cartilage injuries as part of a multiple-repair surgery.

An ACL reconstruction is a procedure that replaces the injured ACL with a tissue graft generally formed from the patient's patellar tendon or hamstring tendon or the ligament of a cadaver. To perform an ACL reconstruction, a surgical procedure is used, typically requiring the multiple steps of harvesting and sizing the tissue graft, securing the tissue graft to the end of a pin, removing the existing damaged ACL, drilling tunnels into the tibial bone and femoral bone, passing the pin and tissue graft through the bone tunnels, screwing an anchor into the femoral bone tunnel and a second anchor into the tibial bone tunnel to capture the tissue graft against the bone and solidly affix the tissue to the bone. Even as an isolated procedure, ACL reconstruction is difficult to perform arthroscopically. Systems recently brought to market still require multiple steps and tools.

SUMMARY OF THE INVENTION

Some embodiments disclosed herein include a tissue anchoring device that comprises an anchor body and a spreader. The anchor body comprises a tubular wall having a constant diameter defining a central bore, a proximal end providing an opening into the central bore, a distal end, and a plurality of compressible tabs located along the tubular wall, wherein each of the compressible tabs is offset axially relative to each other, are bendable between a compressed state and an expanded state, and comprise at least one tooth. The spreader is insertable into the central bore and configured to bend the compressible tabs radially outward relative to the anchor body such that the compressible tabs enter the expanded state upon insertion of the spreader into the central bore.

In some embodiments, the tubular wall lies along a central axis and the compressible tabs extend inwardly beyond the central axis in the compressed state.

In other embodiments disclosed herein the anchor body comprises a tubular wall having a constant diameter defining a central bore, a proximal end providing an opening into the central bore, a distal end, a first row of at least two compressible tabs located along the tubular wall and spaced apart circumferentially and positioned along a first axial position, and a second row of at least two compressible tabs located along the tubular wall and spaced apart circumferentially and positioned along a second axial position. The compressible tabs in the first row are at least partially offset circumferentially relative to each of the compressible tabs in the second row. The compressible tabs comprise at least one tooth and an edge affixed to the tubular wall and is bendable along the edge between a compressed state and an expanded state. The spreader is insertable through the central hole into the central bore and configured to bend the compressible tabs radially outward relative to the anchor body such that the compressible tabs enter the expanded state upon insertion of the spreader into the central bore.

In some embodiments, the compressible tabs in the first row spaced equiangularly about the first axial position, and the compressible tabs in the second row spaced equiangularly about the second axial position. In some embodiments, the first row is comprised of four tabs and the second row is comprised of four tabs. In some embodiments, include a third row of at least two compressible tabs spaced apart circumferentially and positioned along a third axial position, wherein each of the compressible tabs in the third row is at least partially offset circumferentially relative to each of the compressible tabs in the first row and each of the compressible tabs in the second row.

In other embodiments disclosed herein the anchor body comprises a tubular wall having a constant diameter defining a central bore, a proximal end providing an opening into the central bore, a distal end, and a plurality of compressible tabs located along the tubular wall, each of the compressible tabs comprising at least one tooth and having a location on the tubular wall defined by an axial position and a circumferential position, wherein none of the compressible tabs share the axial position of another of the compressible tabs, and none of the compressible tabs share the circumferential position of another of the compressible tabs. The spreader is insertable into the central bore and configured to bend the compressible tabs radially outward relative to the anchor body upon insertion of the spreader into the central bore.

In some embodiments, each of the compressible tabs further comprising an edge affixed to the tubular wall, wherein the edge is configured to allow for pivotal movement of the compressible tabs between a compressed state and an expanded state and the compressible tabs are configured to enter the expanded state upon insertion of the spreader into the central bore. In some embodiments, the compressible tabs are bent inward when in the compressed state such that the anchor body is in a low-profile configuration and the teeth do not extend beyond the tubular wall prior to insertion of the spreader. In some embodiments, the teeth are configured to fixedly secure the anchor body within a bone upon insertion of the spreader into the anchor body. In some embodiments, the anchor body is comprised of a biocompatible engineering polymer material. In some embodiments, the biocompatible engineering polymer material is selected from the group consisting of: polyether-ether-ketone, poly-ether-ketone, polyetherimide, ultrahigh molecular weight polyethylene, polyphenylene, poly(lactide-co-glycolide), and polycaprolactone. In some embodiments, the distal end of the anchor body is rounded. In some embodiments, the distal end of the anchor body comprises a suture loop.

In some embodiments, the tubular wall comprises an inner surface, the spreader is slidably insertable through the proximal end of the anchor body into the central bore, and the spreader is configured to slide against the inner surface. In some embodiments, the spreader and the inner surface of the tubular wall are smooth. In some embodiments, the spreader and the inner surface of the tubular wall comprise complementary textured patterns. In some embodiments, the inner surface of the tubular wall comprises a circumferentially located groove, and the spreader comprises a circumferentially located ridge adapted to fixedly snap within the groove such that the spreader cannot reverse and the anchor body cannot undeploy when the ridge and the groove are engaged.

Some embodiments include a slideable tube positioned over the anchor body, the slideable tube configured to hold the compressible tabs at least partially inside the anchor body until the slideable tube is retracted. In some embodiments, the slideable tube is lubricated to facilitate insertion into a bone and retraction from the anchor body.

Some embodiments disclosed herein include a tissue anchor and inserter combination where the anchoring devices described above are removably coupled to an inserter tool The inserter tool includes a handle, an outer tube coupled to the handle and abutting the spreader, an inner tube or rod positioned within the outer tube and removably coupled to the anchor body, an actuator shaft positioned within the handle and coupled to the inner tube or rod, and a deployment knob coupled to the handle and the actuator shaft and configured to move the actuator shaft relative to the handle and the inner tube relative to the outer tube.

In some embodiments, the inner tube or rod is removably coupled to the distal end of the anchor body. In some embodiments, distal end of the anchor body is rounded and comprises a hole with threads, the threads complementing threads on the inner tube or rod of the insertion tool.

Other embodiments disclosed herein include methods of attaching soft tissue to bone, the method including forming a hole in the bone, inserting the soft tissue into the hole, inserting one of the anchoring devices described above into the hole, and inserting the spreader into the central bore, thereby bending the compressible tabs radially outward to compress the soft tissue against the bone such that the anchoring device and the soft tissue are secured to the bone.

In some embodiments, the bone is a tibial bone. Some embodiments further include drilling a femoral tunnel into a femoral bone, drilling a tibial tunnel into a tibial bone, capturing the soft tissue with a second anchoring device, inserting the second anchoring device and the soft tissue into the femoral tunnel, and securing the soft tissue into the femoral tunnel with a femoral anchor.

BRIEF DESCRIPTION OF THE DRAWINGS

FIGS. 7A-7C depicts three perspective views of one embodiment of a tissue anchoring device in three different stages of a manufacturing process.

FIGS. 10A-10D depicts four frontal views of the bones surrounding the human knee and one embodiment of a method of securing soft tissue to the bones using a tissue anchoring device.

DETAILED DESCRIPTION OF THE CERTAIN EMBODIMENTS

Figure 1A:
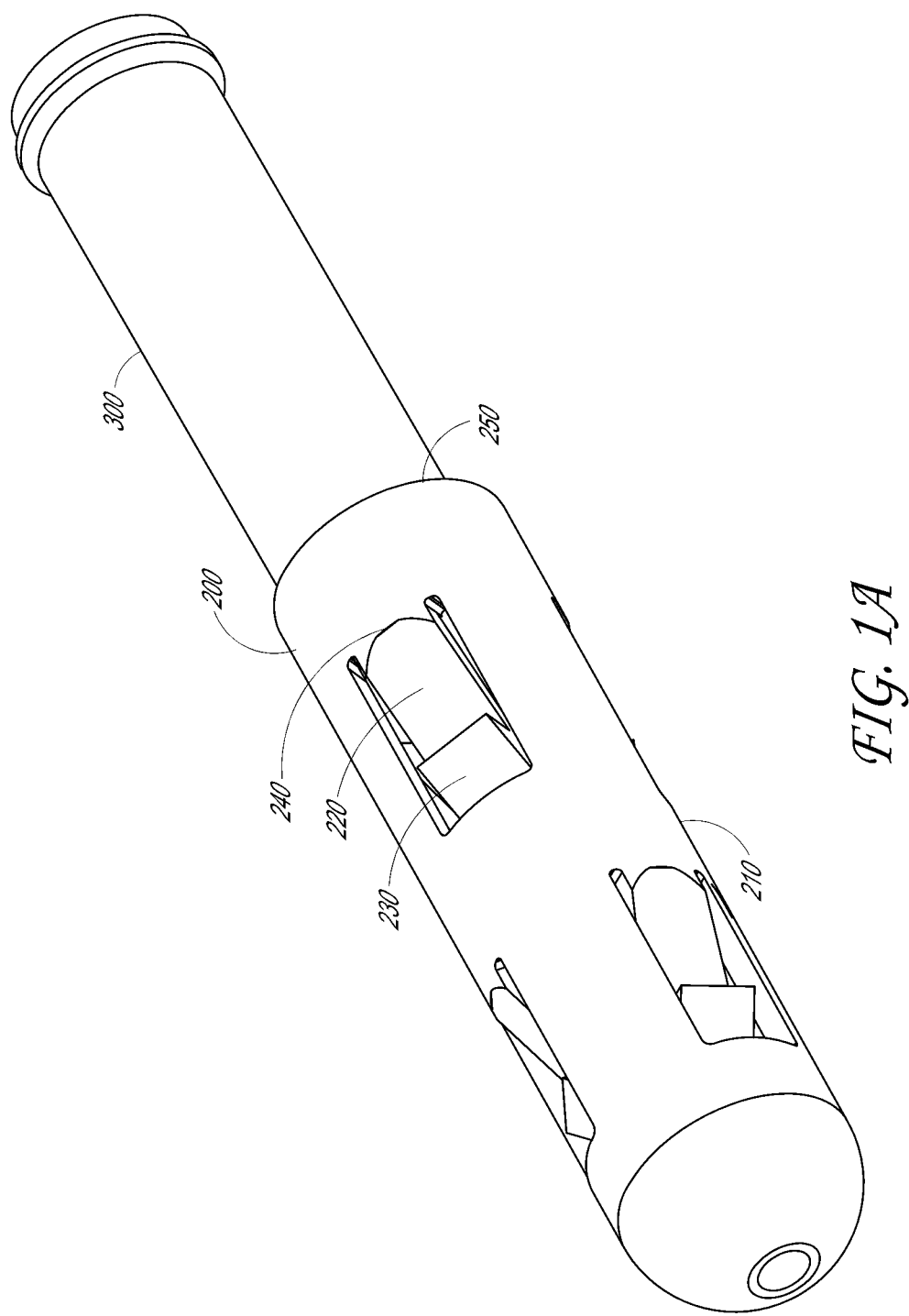
FIG. 1A shows a perspective view of one embodiment of a tissue anchoring device in an undeployed or compressed state.

In various embodiments, soft tissue may be attached to bone utilizing one or more tissue anchoring devices, such a tissue anchoring device 100 depicted in FIG. 1A. The anchor body 200 is comprised of a tubular wall 210 surrounding a central bore and compressible tabs 220. In one embodiment the tubular wall 210 is uniformly tubular in that it comprises a uniform diameter. The compressible tabs are configured to engage with soft tissue and bone, fixedly securing the anchor body 200 and the soft tissue in the bone. In some embodiments, the compressible tabs comprise one or more teeth 230 which are configured to further engage with the tissue and bone. The number of compressible tabs 220 and teeth 230 can vary. The compressible tabs are affixed to the tubular wall along an edge 240. The edge 240 is configured to allow pivotal movement about the tubular wall such that the compressible tabs are bendable between a compressed state and an expanded state. The tissue anchoring device also comprises a spreader 300, which is insertable into the central bore at the anchor body's proximal end 250 and configured to urge the compressible tabs 220 radially outward relative to the tubular wall 210 upon insertion of the spreader into the central bore. In FIG. 1A, the spreader 300 is in its undeployed or uninserted state such that the compressible tabs 220 are collapsed into their compressible state. In the embodiment depicted in FIG. 1A, when the compressible tabs 220 are in their compressed state, the tissue anchoring device 100 is in a streamlined position such that there is little to no protrusion of the teeth 230 radially outward beyond the tubular wall.

Figure 1B:
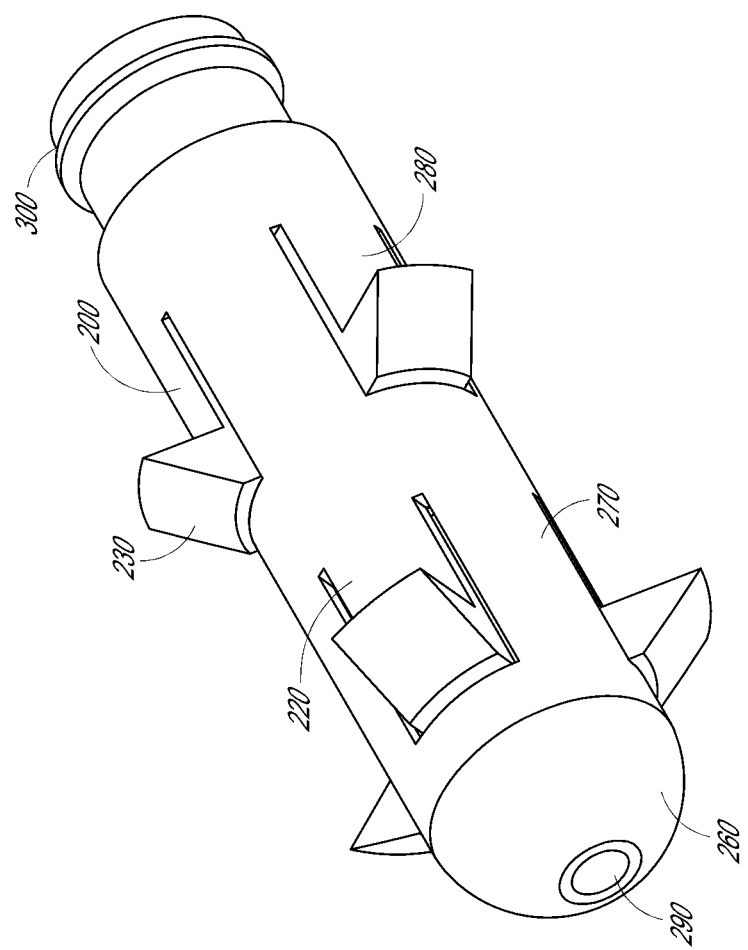
FIG. 1B shows a perspective view of one embodiment of a tissue anchoring device in a deployed or expanded state.

One embodiment of the tissue anchoring device is also depicted in FIG. 1B. FIG. 1B shows a perspective view in which the spreader 300 has been inserted into the central bore of the anchor body 200, thus moving the compressible tabs 220 into their expanded state. In such an expanded state, the teeth 230 extend radially outward from the anchor body 200 and are configured to engage with bone and fixedly secure the tissue anchoring device within the bone. In the embodiment of FIG. 1B, the compressible tabs are positioned along circumferential rows. A first row 270 contains compressible tabs located along a first axial position, and a second row 280 contains compressible tabs located along a second axial position. In some embodiments, the first row of tabs 270 is offset circumferentially relative to the second row of tabs 280 such that no two compressible tabs 220 share the same longitudinal alignment. Such a configuration facilitates capture and fixation of a soft tissue by hindering slippage of the soft tissue between the compressible tabs.

Figure 1C:
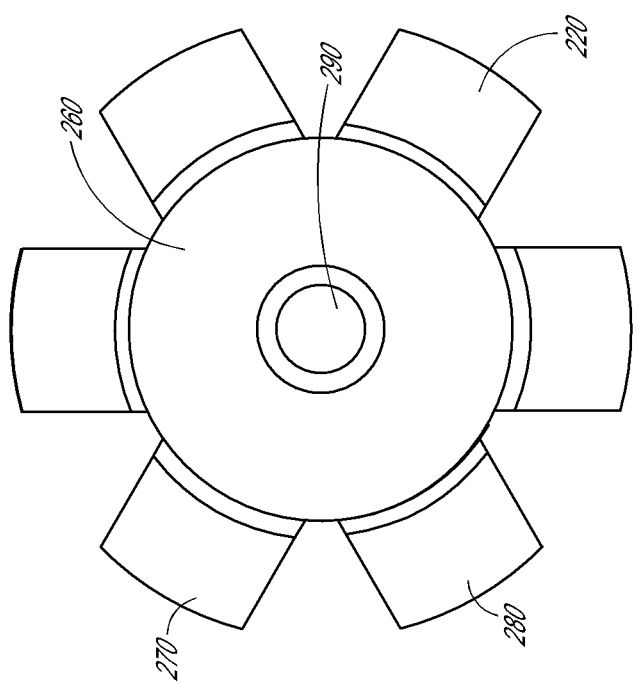
FIG. 1C shows a front view of one embodiment of a tissue anchoring device in the deployed or expanded state.

FIG. 1C provides a front view of the embodiment described in FIG. 1B. FIG. 1C depicts compressible tabs 230 in their expanded state and a first row of compressible tabs 270 offset circumferentially from a second row of compressible tabs 280.

In some embodiments, the distal end 260 of the anchor body is substantially rounded to facilitate insertion of the anchor body into a bone tunnel and to slide around tendon positioned within the bone tunnel. A small hole 290 may advantageously be provided in the center of the distal end 260 to facilitate engagement of the anchor body with an insertion tool, such insertion tool explained in subsequent paragraphs. The small hole 290 may comprise threads to mate with the threads on the inner rod of the insertion tool.

In one embodiment, the tissue anchoring device 100 is made entirely of a biocompatible engineering plastic. Other embodiments include a tissue anchoring device made entirely, or in part, of a biocompatible non-metallic substance. Biocompatible engineering polymer materials such as polyether-ether-ketone, poly-ether-ketone, polyetherimide, ultrahigh molecular weight polyethylene, polyphenylene, poly(lactide-co-glycolide), polycaprolactone, or some other biocompatible polymer material known to those of skill in the art may be used. A non-metallic anchor system may provide certain advantages such as, for example, eliminating MRI artifacts.

Figure 2A:
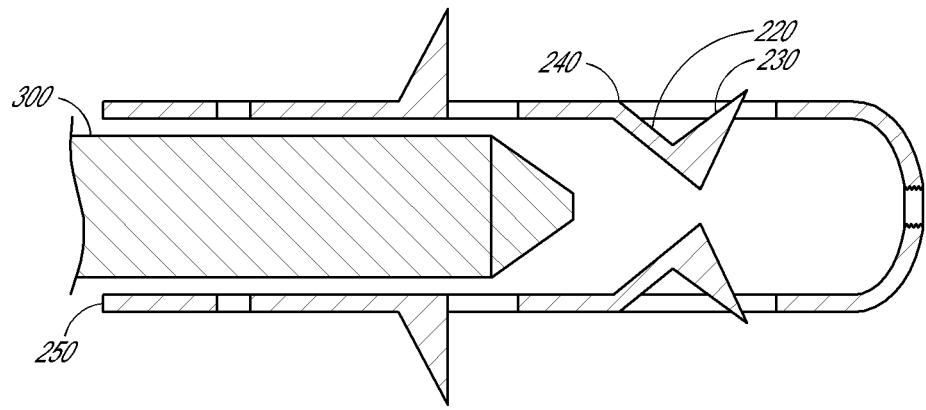
FIG. 2A shows a cross-sectional view of one embodiment of a tissue anchoring device in which the tissue anchoring device has partially deployed or expanded.

In one embodiment of the tissue anchoring device, a plurality of compressible tabs are located along the same axial position, forming circumferential rows of compressible tabs. As shown in the cross-sectional view of FIG. 2A, the compressible tabs move about a hinge-like edge 240, moving from a compressed state to an expanded state upon insertion of the spreader 300 through the proximal end 250 of the anchor body and into the central bore. In the expanded state, the compressible tabs 220 are substantially flush with the tubular wall and the teeth 230 protrude radially outwardly relative to the anchor body.

Figure 2B:
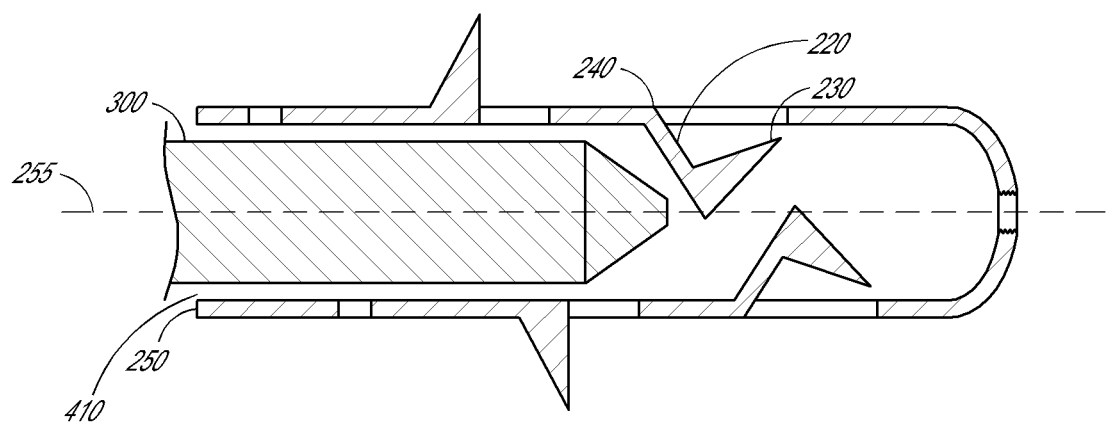
FIG. 2B shows a cross-sectional view of another embodiment of a tissue anchoring device in which the tissue anchoring device has partially deployed or expanded.

In another embodiment of the tissue anchoring device, there exists a plurality of compressible tabs 220, wherein all compressible tabs are offset axially relative to one another. FIG. 2B depicts a cross-sectional view of such an embodiment. With the compressible tabs 220 offset axially, such that no two tabs lie along the same axial position, each tab can be configured to extend beyond the center line or central axis of the central bore when the tab is in its compressed state. Such a configuration allows for the inclusion of larger teeth 230 on the compressible tab than would be possible with many other embodiments, thus facilitating increased contact between the teeth and bone.

Figure 3A:
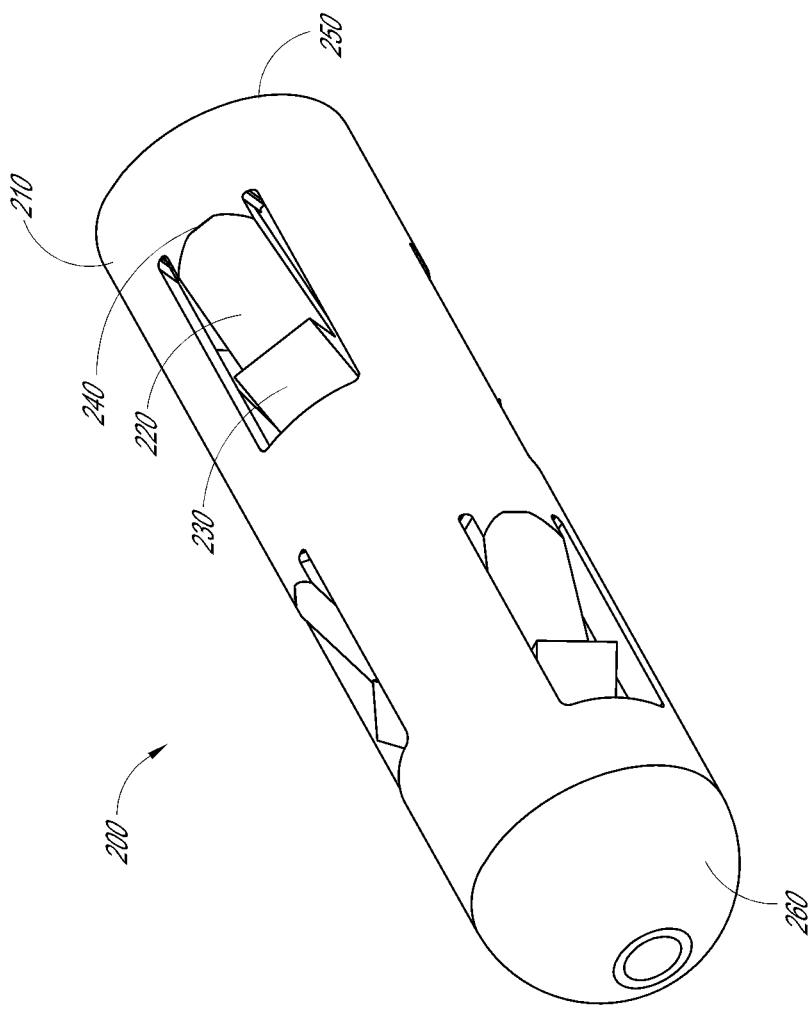
FIG. 3A depicts a perspective distal view of one embodiment of an anchor body in an undeployed or compressed state.

One embodiment, described in the preceding paragraph, is further illustrated in the perspective view provided in FIG. 3A. In FIG. 3A, the anchor body 200 is shown in isolation with the compressible tabs 220 found in their compressed or undeployed state. The anchor body 200 is generally tubular or cylindrical in shape and is comprised of a uniform diameter. The compressible tabs 220 bend inward along the bendable edge 240 such that the teeth 230 are largely retracted into the central bore inside the anchor body and do not extend substantially beyond the tubular wall 210 prior to insertion of the spreader. The compressible tabs 220 are offset both axially and circumferentially relative to each other.

Figure 3B:
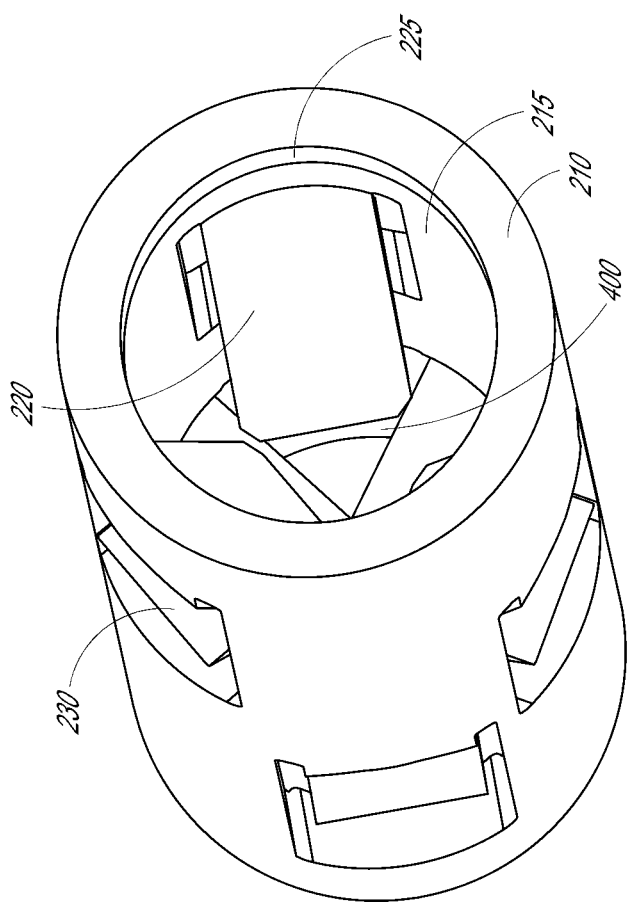
FIG. 3B depicts a perspective proximal view of one embodiment of an anchor body in an undeployed or compressed state.

Another embodiment of a compressed or undeployed anchor body is shown in the perspective view of FIG. 3B. In FIG. 3B, the central bore defined by the tubular wall 210 is visible from the proximal side of the anchor body. The anchor body of this embodiment has an inner surface 215 of the tubular wall which is in contact with a spreader 300 when the spreader is inserted into the anchor body. In some embodiments, the inner surface 215 may be smooth. In other embodiments, in inner surface 215 of the anchor body and the surface of the spreader 300 may not be smooth, but rather, may be textured such as with a scallop shape or grooves so as to inhibit movement of spreader 300 once it is pushed into the anchor body. In some embodiments, texturing in the inner surface 215 is complementary to texturing in the outer surface of the spreader 300.

In the embodiment depicted in FIG. 3B, the inner surface 215 has a circumferentially located groove 225 which engages with a circumferentially located ridge of a spreader upon insertion of the spreader to lock the spreader 300 into place when the anchor body is fully deployed. Such a design prevents unintended retraction or over-insertion of the spreader. The grooved surface 225 is oriented such that the distal end of the spreader 300 can be easily moved in the distal direction in the central bore with the ridge 315 snapping into the groove 225 as the proximal end of the inserter nears the proximal end of the anchor body. In some embodiments, the groove 225 can exist at different locations of the inner surface of the tubular wall 215 or along substantially the entire inner surface 215. In some embodiments, the anchor body 200 may be coupled to the spreader 300 in several positions such that the spreader 300 need not be inserted into the anchor body 200 to its full extent in order to be secured to the anchor body 200. Although a grooved surface is illustrated, it will be appreciated that other shapes are contemplated, including multiple concentric grooves, a series of protruding ridges, or any other suitable structure that permits a spreader 300 to be securely locked within the central bore of the anchor body 200.

Figure 4A:
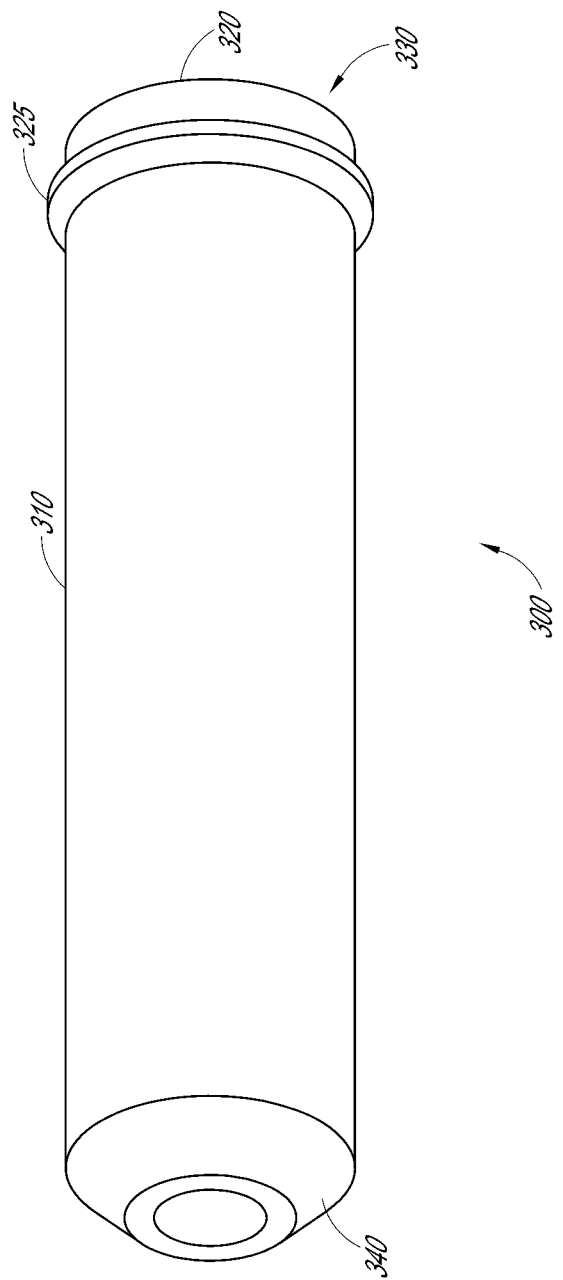
FIG. 4A depicts a perspective distal view of one embodiment of a spreader.
Figure 4B:
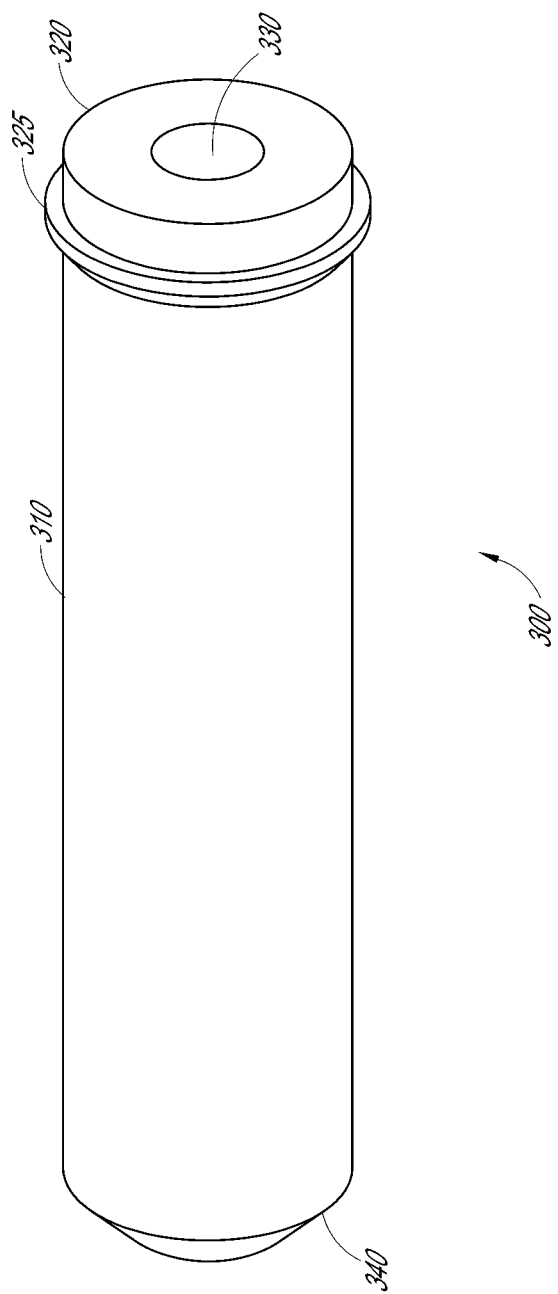
FIG. 4B depicts a perspective proximal view of one embodiment of a spreader.

To provide further details of the spreader, an embodiment of the spreader is depicted in FIGS. 4A and 4B. The spreader 300 may comprise any suitable shape configured to be inserted through the central bore of the anchor body 200. In the embodiment of FIGS. 4A and 4B, the generally tapered distal end 340 of the spreader is configured to come into contact with the compressible tabs of the anchor body and facilitate bending of the tabs into their expanded state upon insertion of the spreader into the anchor body. The body 310 of the spreader is uniformly tubularly shaped and surrounds an axial bore configured for receiving an insertion tool. In this embodiment, the tubular body 310 of the spreader 300 comprises a circumferentially located ridge 325 near its proximal end 320. As the tissue anchoring device is deployed, the spreader 300 is advanced into the anchor body 200, spreading the compressible tabs 220 until the ridge 325 of the spreader 300 engages the groove 225 in the inner surface of the anchor body. In one embodiment, the ridge 315 may be undercut providing even more security against reversing. The proximal end of the spreader comprises a generally flat face and a means for receiving the insertion tool. For instance, in this embodiment, the proximal end 320 of the spreader 300 comprises a hole 330 that receives the insertion tool. After deployment, the spreader remains in the deployed anchor and the insertion tool's inner rod shears off from the anchor body such that the proximal end of the spreader 300 remains in the anchor in a state that is either flush or slightly recessed with respect to the proximal end of the anchor body 200.

The spreader 300 will remain in the anchor body 200 with the compressible tabs 220 in their fully expanded position. The force provided by the interaction between the compressible tabs, teeth and bone keeps the spreader 300 tightly engaged. Further protection against slipping or tilting of the spreader 300 is provided by the optionally ridged sides of the spreader 300. In one embodiment, one or more of the compressible tabs 220 have an indentation on a side facing the central bore. A ridge on the spreader 300 can then engage the indentation, thereby stabilizing the spreader 300 and preventing the spreader 300 from being advanced too far into the anchor. In an alternative embodiment, the spreader 300 comprises an indentation that can engage with a protrusion on a side of a compressible tab facing the central bore. In addition to stabilizing the spreader 300 and preventing over-insertion, this feature also prevents rotation of the spreader 300 relative to the anchor. Inserting the spreader 300 into the anchor body 200 linearly, as opposed to twisting or screwing, is likely to be advantageous in that the linear motion will create no tendency to rotate the anchor. Thus, a linear approach is likely to prevent any twisting or turning of the captured soft tissue.

Figure 5A:
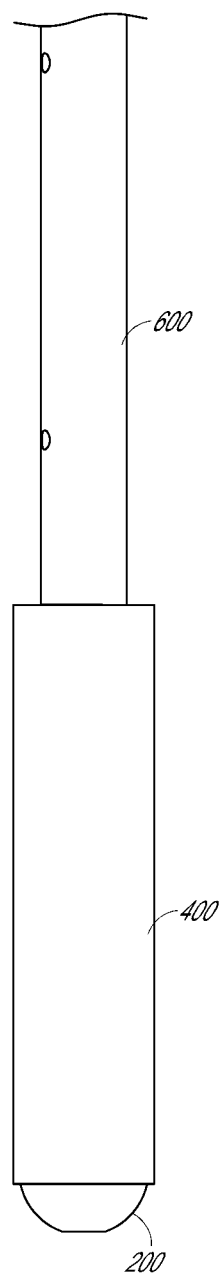
FIG. 5A depicts a side view of one embodiment of a tissue anchoring device attached to an inserter tool and covered by a sleeve.
Figure 5B:
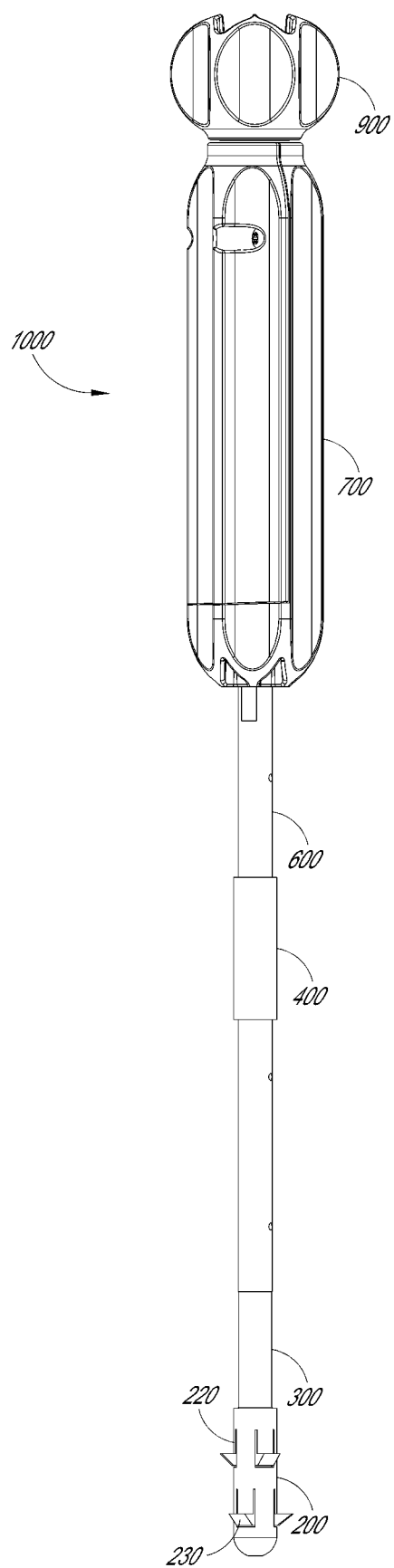
FIG. 5B depicts a perspective view of one embodiment of a tissue anchoring device attached to an inserter tool with the sleeve retracted.

In one embodiment, illustrated in FIGS. 5A and 5B, the compressible tabs may be of a thin enough material thickness such that they can be pushed in by a slidable sleeve 400 positioned over the anchor body 200. The slidable sleeve 400 is configured to hold the compressible tabs 200 in place substantially inside the anchor body 200 during insertion of the anchor body 200 into the bone tunnel. FIG. 5A shows one embodiment of the anchor body 200 and slidable sleeve 400 combination with the anchor body 200 in its compressed state and with the combination connected to the outer tube 600 of the insertion tool. The slidable sleeve 400 can be withdrawn when the anchor body 200 is in place inside a bone, and the compressible tabs will at least partially expand. The compressible tabs and teeth will completely expand according to the method described herein upon insertion of the spreader 300 using the insertion tool 1000. FIG. 5B depicts one embodiment of the anchor body 200 and slidable sleeve combination with the slidable sleeve 400 in a retracted state such that the compressible tabs 220 of the anchor body 200 have partially expanded and the teeth 230 partially protrude radially outward from the tubular wall. In this depiction, the spreader 300 is held adjacent to the anchor body 200 via the inserter tool 1000 prior to insertion of the inserter into the anchor body 200.

Figure 6A:
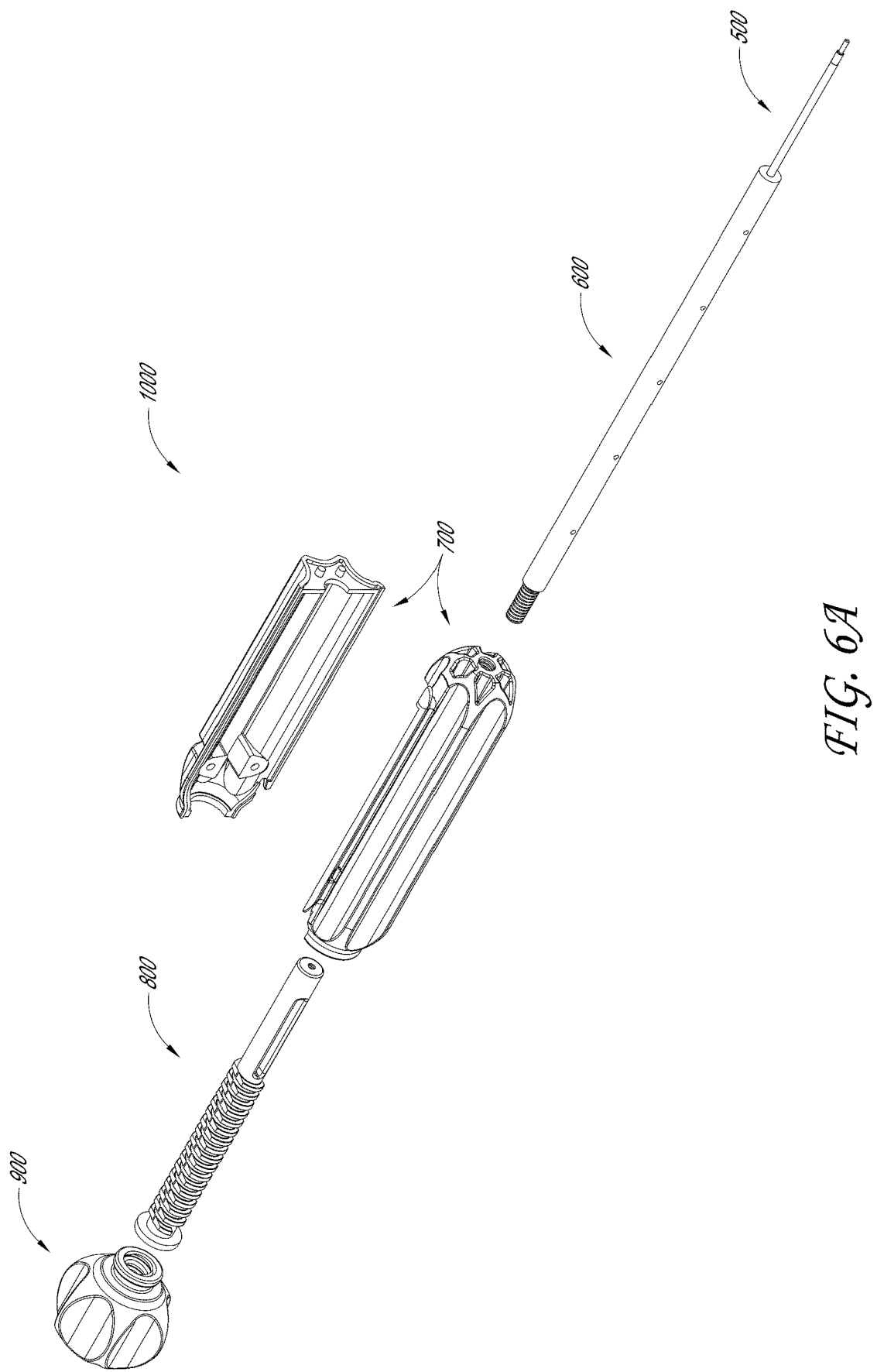
FIG. 6A shows an exploded view of one embodiment of an inserter tool.

FIG. 6A depicts individual components of an inserter tool. The inserter tool 1000 comprises an inner rod or tube 500, an outer tube 600, a handle body 700, a threaded actuator shaft 800, and a deployment knob 900. In some embodiments, the inserter tool 1000 is coupled to the tissue anchoring device 100 during manufacturing. In a preferred embodiment, the inserter tool is disposable.

The inserter tool 1000 is designed to insert and manipulate a tissue anchoring device, such the tissue anchoring device described above. In some embodiments, the tissue anchoring device is manufactured to be attached to an inserter tool before packaging. In other embodiments, the tissue anchoring device is coupled to the inserter tool shortly prior to insertion. In a basic configuration, the inserter tool is assembled as follows: the inserter tool 1000 is configured such that the inner rod 500 is disposed within the outer tube 600. The outer tube is configured to fit against the proximal end of the spreader 300. The inner rod 500 extends through outer tube 600 and is configured to attach to the distal end of the anchor body 200 via threading on both the distal hole in the anchor body 200 and threading on the distal end of the inner rod 500. The proximal end of the outer tube 600 is connected to a handle 700 and the inner rod 500 extends through the proximal end of the outer tube 600 and screws into the threaded actuator shaft 800. The actuator shaft 800 extends just past the proximal end of the handle 700 where it is configured to secure with a deployment knob 900.

The individual components of the inserter tool are further described in detail below.

Figure 6B:
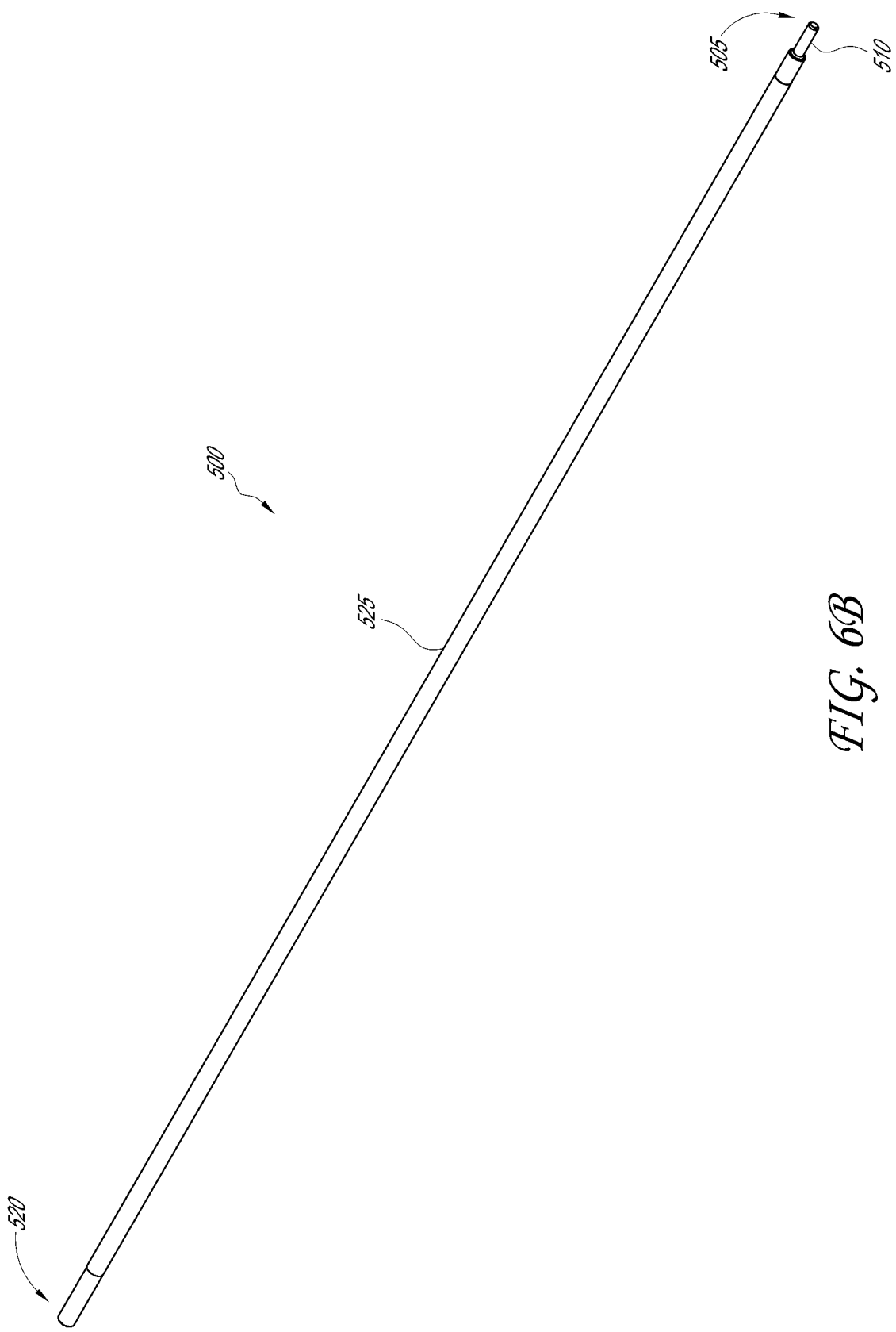
FIG. 6B shows a perspective view of one embodiment of an inner rod component of an insertion tool.

FIG. 6B shows a perspective view of an embodiment of the inner rod 500. In some embodiments, the inner rod is an inner tube. The inner rod comprises a rodlike or tube-like body 525, a distal end 510 configured to secure to the spreader 300, and a proximal end 520 which is configured to interact with the other components of the inserter such as the actuator shaft 800. The inner rod 500 is configured such that a proximal end 520 is advanced through the outer tube 600 and into the handle 700 where it is further secured within the actuator shaft 800 via threading. The distal end of the inner rod 500 is configured to extend through the central bore in the spreader 300 and the anchor body 200 and then be secured to the distal end of the anchor body 200. Upon activation, the inner rod is retracted until the tissue anchoring device is fully deployed and the inner rod is separated from the anchor.

The inner rod 500 extends through the central bore in the spreader 300 and the anchor body 200 before coupling with the distal end of the anchor body 200. In one embodiment, the inner rod 500 couples with the anchor body 200 through threads 505 on the end of the inner rod 500 and within the distal end of the anchor body 200. In other embodiments, the inner rod 500 may couple to the anchor body 200 through other securing mechanisms such as adhesives, welding or frictional fit.

Figure 6C:
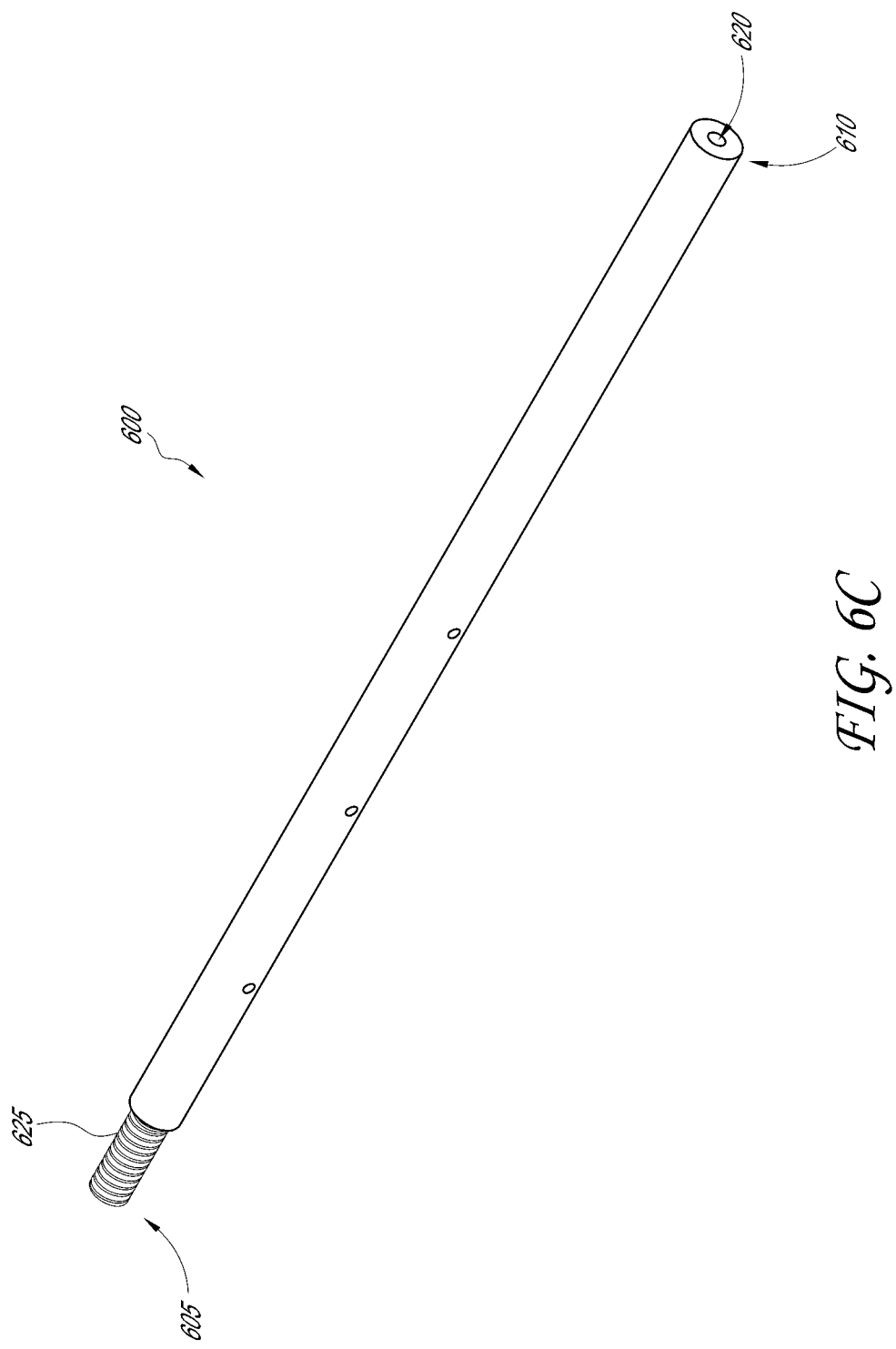
FIG. 6C shows a perspective view of one embodiment of an outer tube component of an insertion tool.

FIG. 6C shows an embodiment of the outer tube 600. The outer tube 600 is attached at its proximal end 605 to the distal end of handle 700 via threading 625. The distal end 610 of the outer tube 600 is configured such that the inner rod 500 can be drawn into the outer tube 600 through the distal end 610 of outer tube 600. When the inner tube 500 is advanced far enough that the spreader 300 locks into place or cannot advance anymore, the distal surface of the outer tube 600 may be level with the proximal surface of the anchor body 200. When the inner rod 500 withdraws further into the outer tube upon the continued rotation of the deployment knob and advancement of the actuator shaft, the inner rod 500 strips the threading from the anchor body 200 and the inserter tool 400 detaches from the anchor.

Figure 6D:
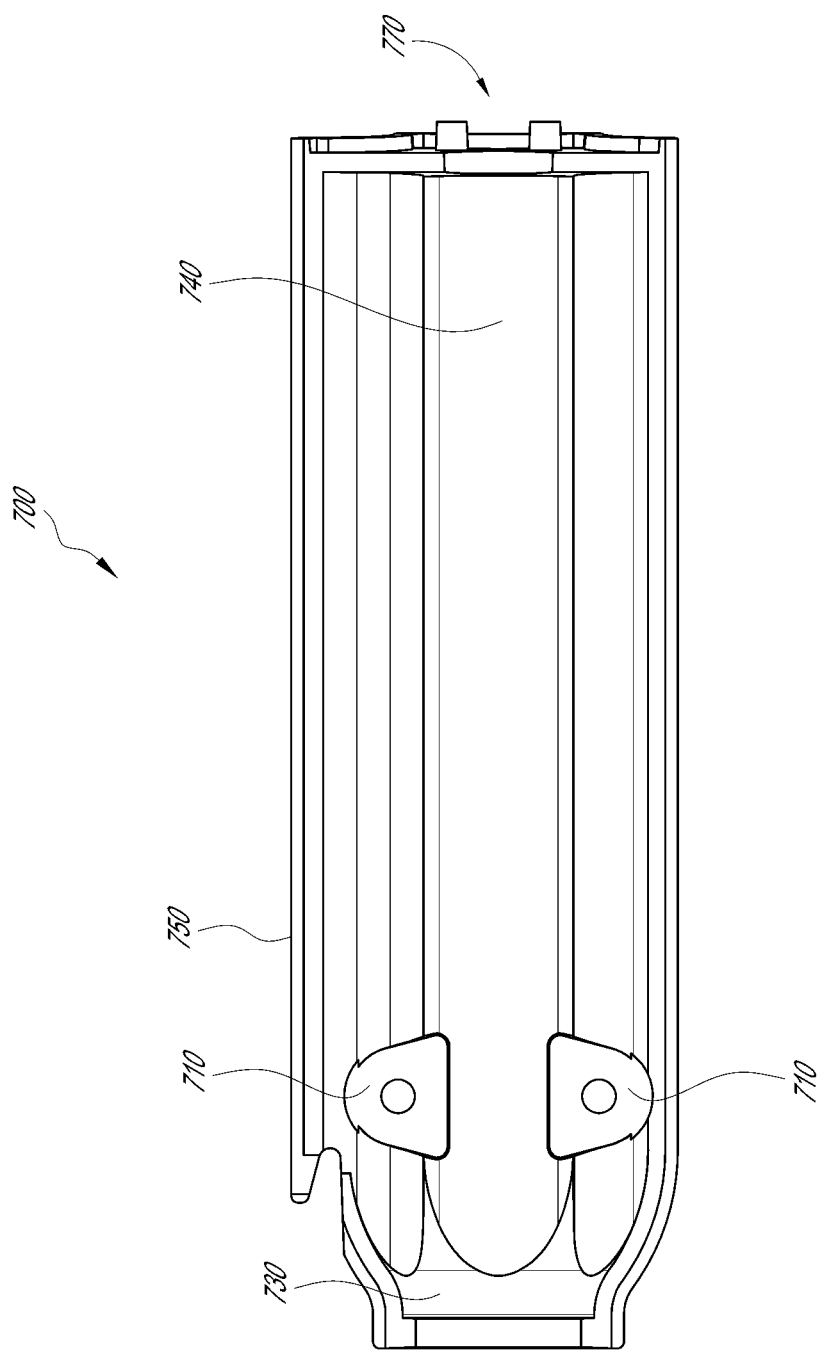
FIG. 6D shows a side view of one embodiment of a handle component of an insertion tool.
Figure 6E:
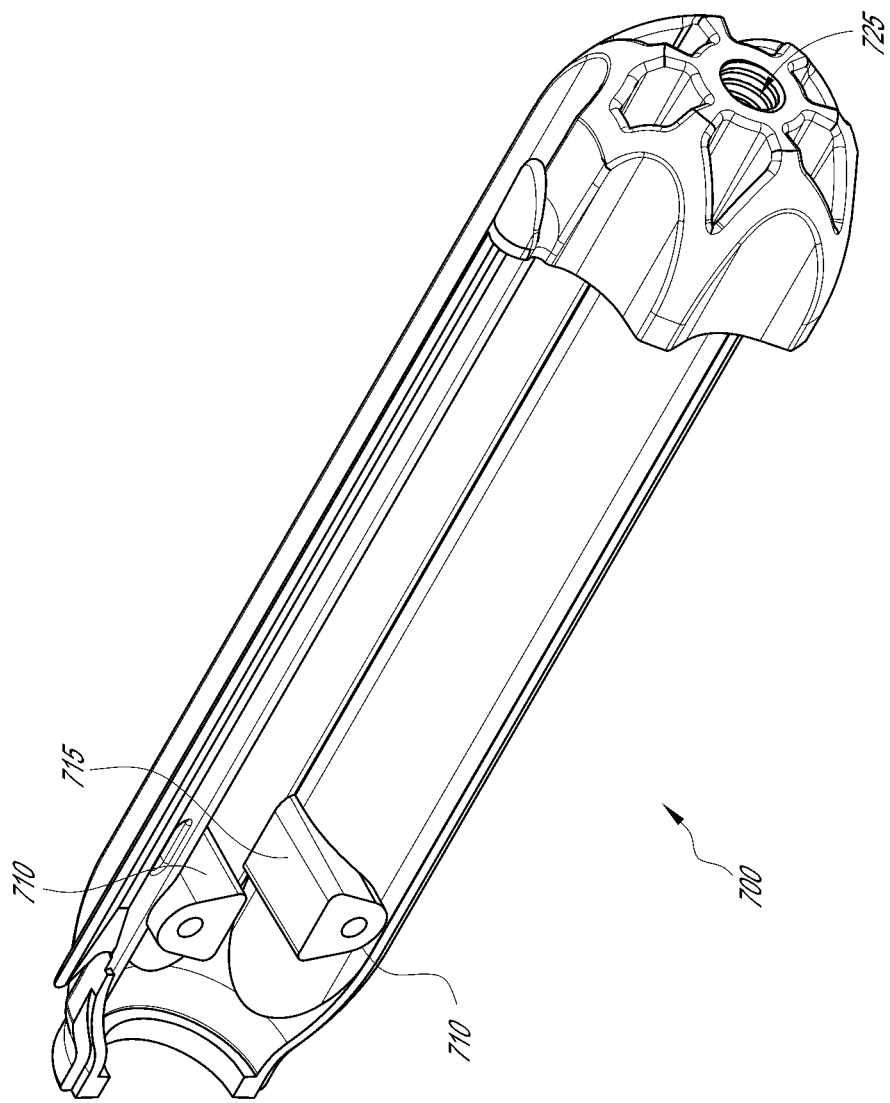
FIG. 6E shows a perspective view of one embodiment of a handle component of an insertion tool.

FIGS. 6D and 6E show embodiments of a handle body 700. FIG. 6D is a cross-sectional view of one embodiment of a handle 700 and 6E is a cut-away view of the handle body 700. The proximal end of the handle 700 is configured to receive the deployment knob 900 via the ridges 730 which hold the knob 900 secure. The actuator shaft 800 is housed within the handle body 700. A set of brackets or braces 710 each having a flat surface 715 secure the actuator shaft 800 within the handle 700. The distal end 770 of the handle is configured to receive the outer tube 600 via threads 725 in opening 740. The outer tube 600 is permanently affixed to the handle 700 at its distal end.

Figure 6F:
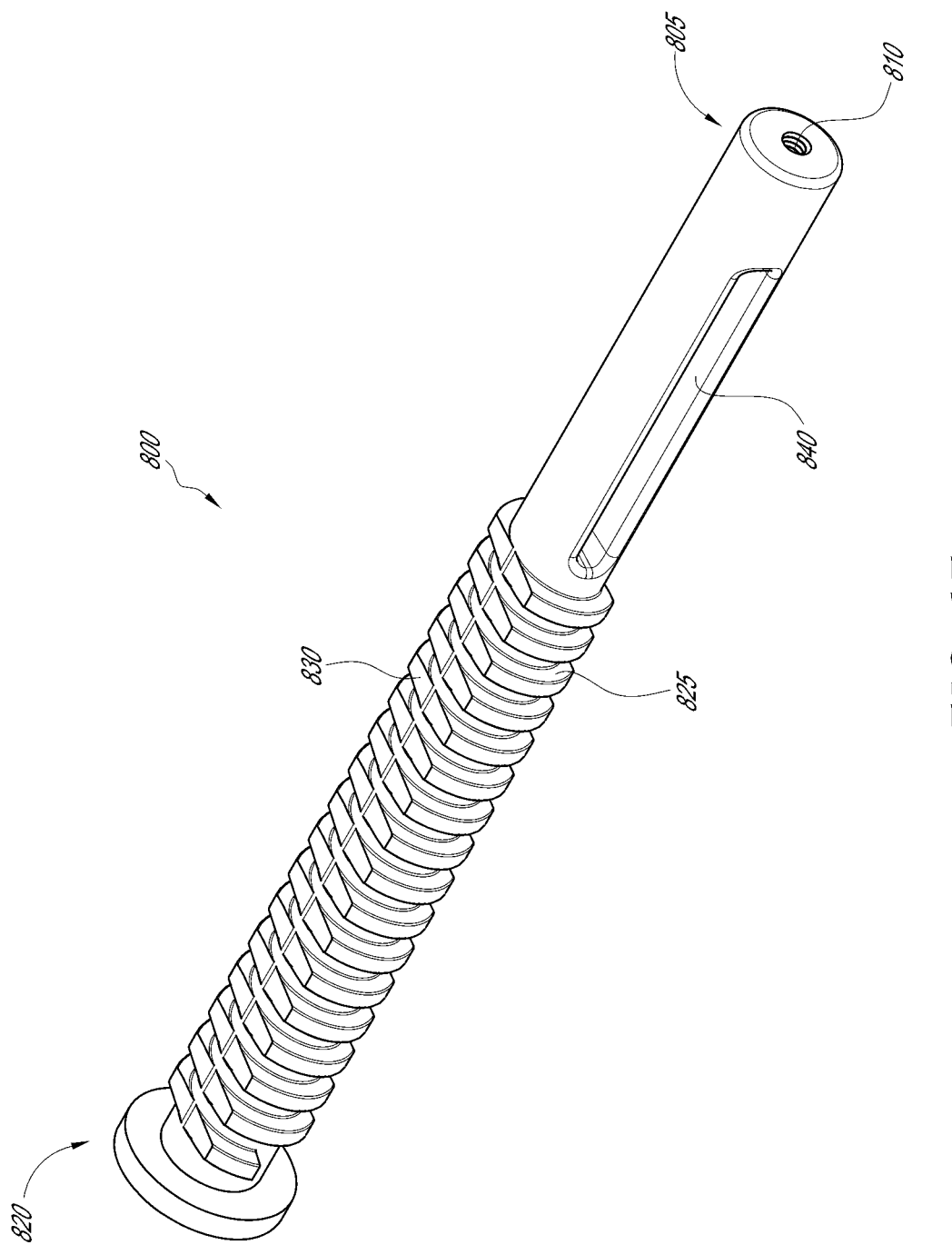
FIG. 6F shows a perspective view of one embodiment of an actuator shaft component of an insertion tool.

FIG. 6F depicts the threaded actuator shaft 800. The actuator shaft 800 is comprised of a distal end 805 comprising a threaded hole 810 which is configured to receive the inner rod 500, a second threaded portion 825 on the body of the shaft configured to advance the inner rod 500, and a proximal end 820 configured to secure within the deployment knob 900. The threading 825 of the actuator 800 has two flat areas 830, one on each side, where there is no threading. These flat areas 830 fit within the flat brackets 710 of the handle such that the actuator 800 cannot rotate within the handle.

The body of the actuator shaft 800 is configured with threading 825 to permit the shaft 800 to advance the inner tube 500. The body of the actuator shaft 800 is not perfectly round, but rather is oval shaped with flat sides 830 that fit into the handle body 700 in such a way that the actuator shaft 800 cannot itself rotate when the deployment knob 900 is turned and the shaft 800 advances via knob 900. Thus, the threads do not go all the way around the shaft but rather flatten out on the flattened sides of the shaft. The actuator shaft is configured as a coaxial system. That is, the spreader 300, inner tube 500 and actuator 800 are configured to operate as one piece. The flat brackets 710 in the handle make the actuator shaft 800 stay on plane such that the actuator shaft 800 itself cannot rotate within the handle 700. The proximal end of the inner tube 500 couples with the distal end of the actuator shaft 800 via threading.

Figure 6G:
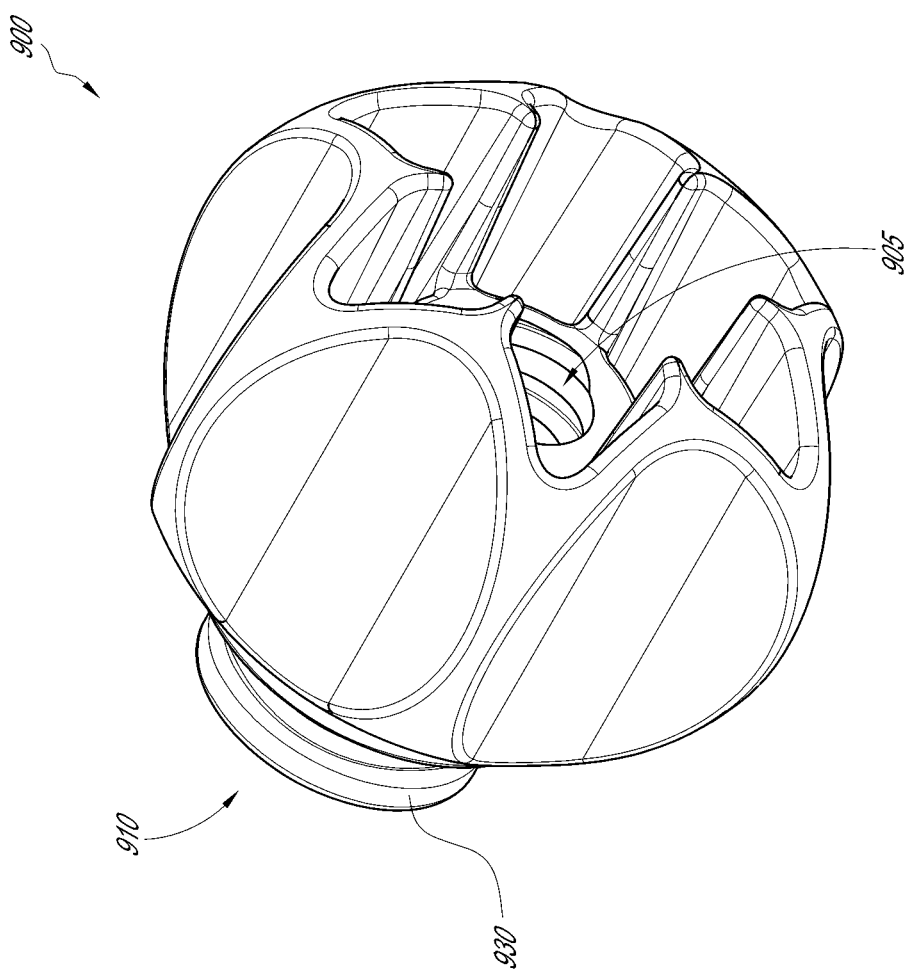
FIG. 6G shows a perspective view of one embodiment of a deployment knob component of an insertion tool.

FIG. 6G depicts a deployment knob 900. The deployment knob 900 comprises a central hole 910 which is configured with threading 905, and a groove 930 configured to be received by a corresponding ridge 730 of the handle 700. The threading 905 in the central hole 910 is configured to receive the actuator shaft 800. The deployment knob 900 is configured to advance, relative to the deployment knob 900, the inner rod 500 via the actuator shaft 800. The actuator shaft 800 is joined at its proximal end to the distal end of the deployment knob 900 via threading 905 in the central hole 910. The actuator shaft 800 is attached to the inner rod 500 by way of the proximal end of the inner rod 500 advancing into the distal end of the actuator shaft via threading so that when the deployment knob 900 is rotated, the mechanism of the shaft 800 advances the inner rod 500 proximally such that the spreader 300 is then advanced into the anchor body 200 to expand the anchor body 200 into bone and secure the tissue anchoring device.

In one embodiment, the deployment knob 900 is threaded 905 to receive the actuator shaft via the groove 930 of knob 900 fitting with the proximal end ridge 730 of the handle body 700. As the deployment handle is turned, the actuator shaft 800 is advanced in a proximal direction until the anchor body 200 is deployed and locked into place.

When in the position for deployment, the inner rod 500 is positioned within the outer tube 600, and the outer tube is flush with the anchor body 200. The inner rod 500 may hold the anchor body 200 steady during insertion and deployment. The inner rod 500 extends through the spreader 300 and couples to the anchor body 200 via threading. The spreader 300 is configured to be advanced distally through the proximal end of the anchor body 200 by the retraction of the inner rod 500 via rotating the deployment knob 900, which pulls the anchor body 200 proximally relative to the spreader 300.

The outer tube 600 provides the mechanism to push the spreader 300 into the central hole 225 in the anchor body 200 to fully expand the anchor body 200. During deployment of the tissue anchoring device, the inner rod 500 is continually retracted via a screwing motion until the spreader 300 locks into the anchor body 200. As the deployment knob 900 continues to turn and the inner rod 500 continues to pull on the threads of the anchor body 200, the inner rod 500 strips the threads from the inside of the anchor body 200 and the insertion tool 400 releases from the anchor body 200. Any thread shavings are contained within the outer tube 600.

In some embodiments, a pre-attached delivery handle is provided. In some embodiments, the insertion tool or delivery handle is disposable. In other embodiments, the insertion tool can be sterilized, reloaded, and reused.

Those of skill in the art will appreciate other inserters and mechanisms that may be used to insert and deploy the tissue securing anchor described herein. Although a particular insertion device for inserting and manipulating a tissue anchoring device has been described, it should be understood that other inserter designs may be used for manipulating the tissue anchoring device described above in order to insert the anchor and soft tissue into bone. For example, it may be possible to use separate tools for inserting the anchor, securing soft tissue, and securing the anchor.

The anchors described above may be manufactured using any suitable technique. In one embodiment, the anchor body 200 comprising compressible tabs 220 is manufactured as depicted in FIGS. 7A-7C. First, as depicted in FIG. 7A, the tubular wall 210 with central bore is manufactured using traditional machining techniques. For example, PEEK rod stock may be machined to form the anchor body depicted in FIG. 7A. A series of ridges 235 surrounding the tubular wall 210 are produced with machining. The ridges 235 serve as precursors to the teeth 230 on compressible tabs 220. The teeth 230 are produced as depicted in FIG. 7B by machining away portions of the ridges 235. Finally, as depicted in FIG. 7C, slots 245 are cut into the tubular wall 210 to form the three sides of the compressible tabs 220. The slots 245 may be formed using any suitable technique, for example, laser etching. Depending on the desired configuration of the compressible tabs 220 in the non-deployed state, manufacturing may be complete after forming the tabs 220 as depicted in FIG. 7C. For example, in embodiments utilizing an outer sleeve to compress the tabs 220, no further processing may be required. In other embodiments, the tubular wall 210 can be heated and the compressible tabs 220 compressed into central bore, such as by using a sleeve slid over the anchor body 200. Upon cooling, the tabs 220 will maintain their compressed position until a spreader is inserted into the central bore to deploy the tabs 220.

The anchors described above may be used to secure a tissue graft in an ACL repair. In some embodiments, the anchors described above are used to anchor tissue in a bone tunnel in the tibia. In such procedures, the tissue graft is first anchored within a bone tunnel in the femur. Any suitable anchor may be used to secure tissue to the femur. In some embodiments, suitable anchors include a tissue grasping feature that can be used to capture tissue and feed it through bone tunnels in the tibia and/or femur. In some embodiments, the tissue grasping feature includes a suture loop that can be tightened around one or more strands of tissue.

Figure 8A:
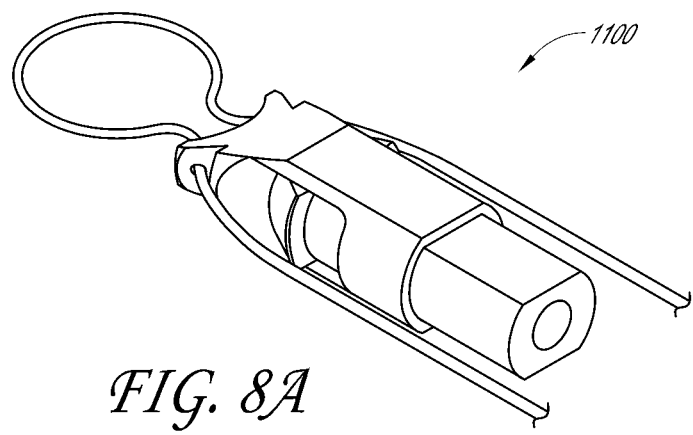
FIG. 8A shows a perspective view of one embodiment of a femoral tissue capture anchor device in an undeployed or unexpanded state.
Figure 8B:
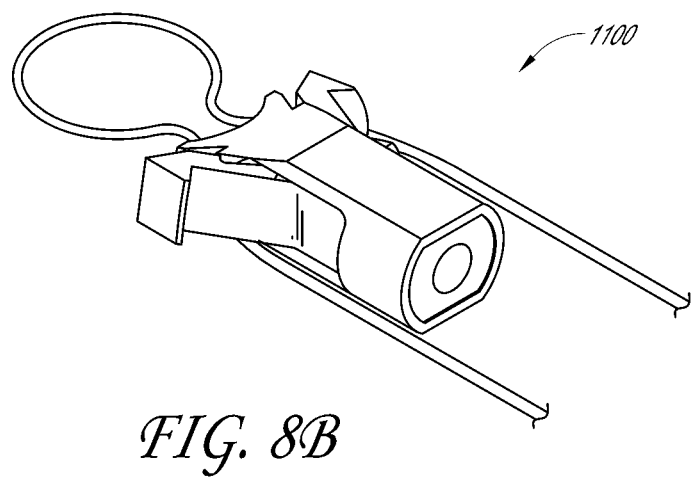
FIG. 8B shows a perspective view of one embodiment of a femoral tissue capture anchor device in a deployed or expanded state.

One example of such a suture loop anchor 1100 is depicted in FIGS. 8A and 8B and described in more detail in FIGS. 13A-16B in U.S. Patent Application Publication No. 2011-0112550, which is incorporated herein by reference in its entirety. FIG. 8A depicts the femoral anchor 1100 in an undeployed state with suture loop ready to capture tissue. After tissue capture and insertion in the femur, lateral protrusions on the anchor 1100 may be deployed to secure the anchor and issue into the femur. FIG. 8B depicts the femoral anchor 1100 in its deployed state.

Figure 9:
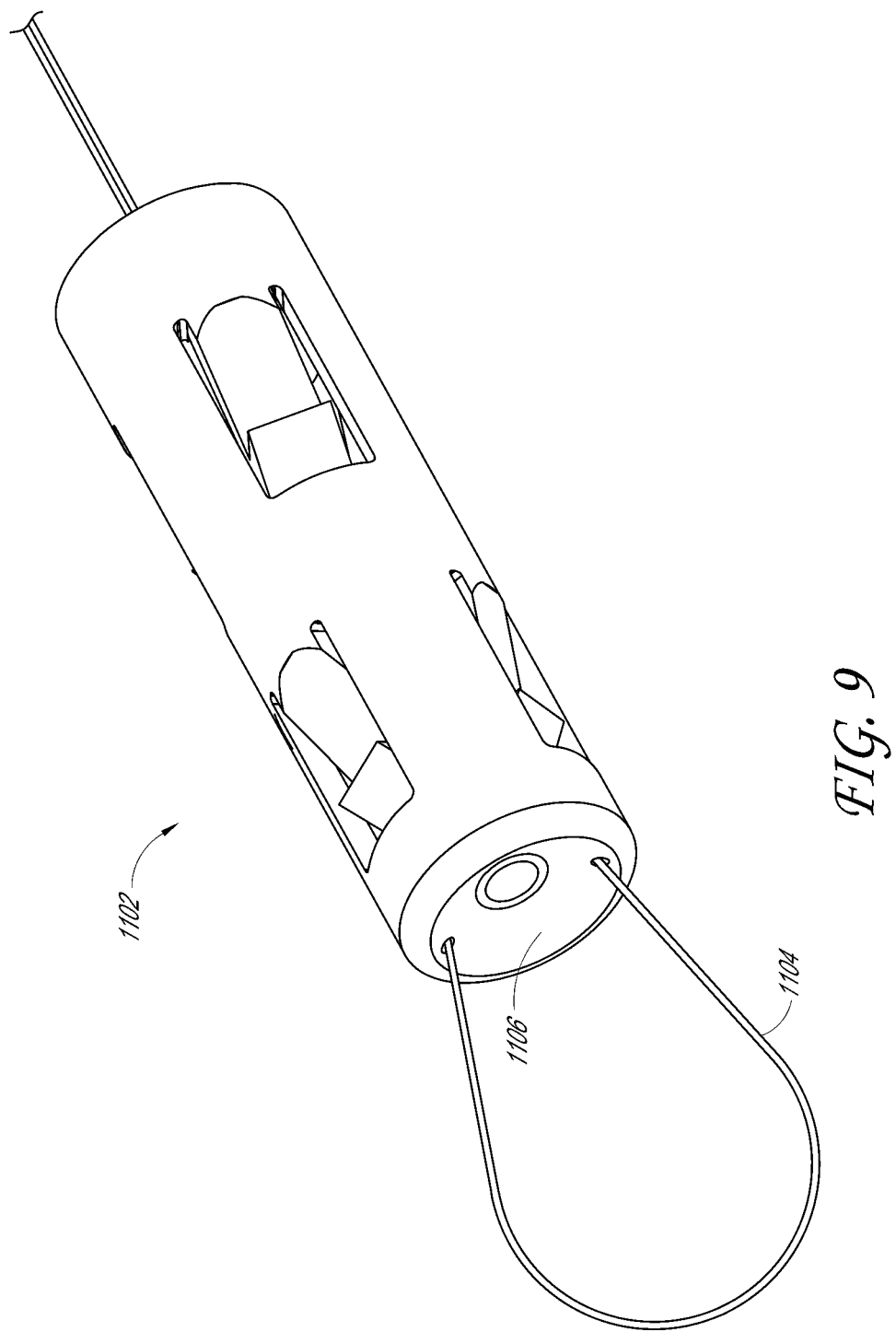
FIG. 9 shows a perspective view of one embodiment of a tissue anchoring device comprising a tissue capture suture loop.

In other embodiments, a modified version of the tibial anchor described above may be used as the femoral anchor. One such embodiment is depicted in FIG. 9. In this case, instead of a rounded distal end, the anchor body 1102 comprises a flat, depressed, or saddle shaped distal end 1106. Two apertures or provided in the distal end 1106 to accommodate the treading of a suture to form a suture loop 1104 in the distal end. As in the anchor described in FIGS. 8A and 8B, tissue may be captured within the suture loop 1104, the suture tightened, and then the anchor 1102 with captured tissue inserted into the femoral bone tunnel. The anchor 1102 may be deployed using the same spreader and inserter as described above for the tibial anchor.

Those of skill in the art will appreciate other suitable femoral anchors for use in combination with the tibial anchor described herein in performing an torn ACL repair.

FIGS. 10A-10D depict some non-limiting suitable ACL repair techniques utilizing the anchors described herein. First, as depicted in FIG. 10A, bone tunnels 1110 and 1120 are formed in the tibia and femur. In some embodiments, both tunnels 1110 and 1120 are formed using a single drill drilling through the tibia and then into the femur. In other embodiments, the femoral tunnel 1110 and tibial tunnel 1120 may be formed separately. Next, a surgeon obtains a suitable tissue graft 1130, which may include tendon from the patient (e.g., one or more patellar or hamstring tendons), from a cadaver, or a synthetic graft. The tissue graft 1130 is then captured by a femoral anchor 1100, such as the anchors described in FIGS. 8A-9. The femoral anchor 1100 is then inserted into the femoral tunnel 1110 and deployed to secure the graft 1130 into the femur.

In one embodiment, as depicted in FIG. 10B, a lateral technique is used whereby the surgeon inserts the femoral anchor 1100 with captured tissue graft 1130 laterally into the space between the femur and tibia. The femoral anchor 1100 is then inserted directly into the femoral bone tunnel 1110. The joint may be abducted to facilitate direct insertion in the femoral tunnel 1110. After insertion of the femoral anchor 1100, the tissue graft 1130 may then be fed down through the tibial bone tunnel 1120 and out the other side resulting in the configuration depicted in FIG. 10C. In one technique, a suture loop is fed up through the tibial tunnel 1120, the graft 1130 is fed through the loop, and then the loop is pulled back through the tibial tunnel 1120, drawing the graft 1130 with it.

In an alternative embodiment, an in-line approach may be used where the femoral anchor 1100 with captured tissue graft 1130 is inserted through the tibial bone tunnel 1120 and then into the femoral bone tunnel 1110. The result is graft running from the femoral anchor 1100 through and out of the tibial tunnel 1120 as depicted in FIG. 10C.

After achieving the configuration of FIG. 10C, the joint may be position and the tissue graft 1130 tensioned as appropriate. Next, as depicted in FIG. 10D, a tibial anchor 100 as described herein may be inserted into the opening of the tibial bone tunnel 1120 and deployed to secure the graft 1130 to the tibia. Excess graft 1130 may then be trimmed to be flush with the tibial anchor 100.

In some embodiments, the approach described above is conducted using a single strand of tissue graft 1130. In this case, the graft 1130 may be captured by the femoral anchor 1100 and doubled over the end of the anchor anchor such that two parallel portions of the graft 1130 run from the femoral anchor 1100 to the tibial anchor 100. In other embodiments, two strands of tissue graft 1130 may be doubled over the end of the femoral anchor 1100 resulting in four parallel portions of graft 1130 running from the femoral anchor 1100 to the tibial anchor 100.

Although ACL repair techniques have been described herein, it will be appreciated that the anchors described may be used in any number of procedures where a surgeon desires to fix soft tissue to bone.

Although the invention has been described with reference to embodiments and examples, it should be understood that numerous and various modifications can be made without departing from the spirit of the invention. Accordingly, the invention is limited only by the following claims.

What is claimed is:

1. A tissue anchor and inserter combination, comprising:
 an anchoring device removably coupled to an inserter tool, the anchoring device comprising an anchor body comprising:
  a tubular wall having a constant diameter defining a central bore, a proximal end providing an opening into said central bore,
  a distal end, and a plurality of compressible tabs located along said tubular wall, each of said compressible tabs comprising at least one tooth and having a location on said tubular wall defined by an axial position and a circumferential position,
  wherein all of the compressible tabs are offset circumferentially from one another so that none of the compressible tabs share a same longitudinal alignment, or all of the compressible tabs are offset axially so that none of the compressible tabs lie along a same axial position;
  and a spreader insertable into said central bore and configured to bend said compressible tabs radially outward relative to said anchor body upon insertion of said spreader into said central bore;
 wherein the inserter tool comprises:
  a handle,
  an outer tube coupled to said handle and abutting said spreader,
  an inner tube or rod positioned within said outer tube and removably coupled to said anchor body, an actuator shaft positioned within said handle and coupled to said inner tube or rod, and a deployment knob coupled to said handle and said actuator shaft and configured to move said actuator shaft relative to said handle and said inner tube relative to said outer tube.

2. The combination according to claim 1, wherein said inner tube or rod is removably coupled to said distal end of said anchor body.

3. The combination according to claim 1, wherein said distal end of said anchor body is rounded and comprises a hole with threads, said threads complementing threads on said inner tube or rod of said insertion tool.

4. The device according to claim 1, each of said compressible tabs further comprising an edge affixed to said tubular wall, wherein said edge is configured to allow for pivotal movement of said compressible tabs between a compressed state and an expanded state and said compressible tabs are configured to enter said expanded state upon insertion of said spreader into said central bore.

5. The device according to claim 2, wherein said compressible tabs are bent inward when in said compressed state such that said anchor body is in a low-profile configuration and said at least one tooth of each of said compressible tabs do not extend beyond said tubular wall prior to insertion of said spreader.

6. The device according to claim 1, wherein said at least one tooth of each of said compressible tabs are configured to fixedly secure said anchor body within a bone upon insertion of said spreader into said anchor body.

7. The device according to claim 1, wherein said anchor body is comprised of a biocompatible engineering polymer material.

8. The device according to claim 7, wherein said biocompatible engineering polymer material is selected from the group consisting of: polyether-ether-ketone, poly-ether-ketone, polyetherimide, ultrahigh molecular weight polyethylene, polyphenylene, poly(lactide-co-glycolide), and polycaprolactone.

9. The device according to claim 1, wherein said tubular wall comprises an inner surface, said spreader is slidably insertable through said proximal end of said anchor body into said central bore, and said spreader is configured to slide against said inner surface.

10. The device according to claim 9, wherein said spreader and said inner surface of said tubular wall are smooth.

11. The device according to claim 9, wherein said spreader and said inner surface of said tubular wall comprise complementary textured patterns.

12. The device according to claim 9, wherein said inner surface of said tubular wall comprises a circumferentially located groove, and said spreader comprises a circumferentially located ridge adapted to fixedly snap within said groove such that said spreader cannot reverse and said anchor body cannot undeploy when said ridge and said groove are engaged.

13. The device according to claim 1, further comprising a slideable tube positioned over said anchor body, said slideable tube configured to hold said compressible tabs at least partially inside said anchor body until said slideable tube is retracted.

14. The device according to claim 13, wherein said slideable tube is lubricated to facilitate insertion into a bone and retraction from said anchor body.

15. The device according to claim 1, wherein said distal end of said anchor body comprises a suture loop.

* * * * *